United States Patent [19]

Watanabe et al.

[11] Patent Number: 4,841,044
[45] Date of Patent: Jun. 20, 1989

[54] CEPHALOSPORIN DERIVATIVES

[75] Inventors: Yoshiaki Watanabe, Kodaira; Chihiro Yokoo, Gyoda; Masami Goi, Kisai; Akira Onodera, Kuki; Mitsuo Murata, Washimiya; Hiroshi Fukushima, Miyashiro; Minoru Taguchi, Ohmiya; Kaoru Sota, Shimotomi, all of Japan

[73] Assignee: Taisho Pharmaceutical Co., Ltd., Japan

[21] Appl. No.: 943,037

[22] Filed: Dec. 18, 1986

[30] Foreign Application Priority Data

Dec. 23, 1985 [JP] Japan .............................. 60-289589
Mar. 15, 1986 [JP] Japan .............................. 61-56084
Jun. 25, 1986 [JP] Japan .............................. 61-148668

[51] Int. Cl.⁴ ................ C07D 501/36; A61K 31/545
[52] U.S. Cl. ................................. 540/227; 540/226; 514/204; 514/206
[58] Field of Search .................. 540/226, 227, 222

[56] References Cited

U.S. PATENT DOCUMENTS 4,699,981 10/1987 Watanabe et al. ............... 540/226

FOREIGN PATENT DOCUMENTS 2144420A 3/1985 United Kingdom .

Primary Examiner—Nicholas S. Rizzo
Attorney, Agent, or Firm—Lorusso & Loud

[57] ABSTRACT

Cephalosporin derivatives represented by the general formula

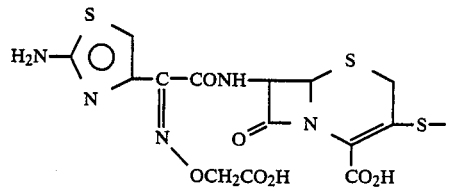

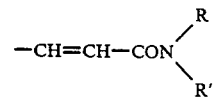

wherein R is a hydrogen atom or a lower alkyl group having 1 to 4 carbon atoms, R' is a hydrogen atom, a lower alkyl group having 1 to 4 carbon atoms, a cycloalkyl group having 5 or 6 carbon atoms or a benzyl group, or R and R' together with the nitrogen atom to which they are attached form a tetrahydropyridinyl group, a morpholinyl group or pyrroridinyl group, and the non-toxic salts thereof are disclosed. These compounds are useful as antibacterial agents.

5 Claims, No Drawings

CEPHALOSPORIN DERIVATIVES

BACKGROUND OF THE INVENTION

1. Field of the Invention

The present invention relates to novel cephalosporin derivatives for oral administration, and more particularly to cephalosporin derivatives and their non-toxic salts showing excellent antibacterial effect by oral administration.

2. Description of the Prior Art

Cephalosporin drugs are widely used for the treatment and prevention of various infectious diseases caused by pathogenic bacteria.

Especially, since the cephalosporin drugs for oral administration, represented by cefalexin, can be more easily used than the cephalosporin drugs for injectional administration, they are most widely used now. Compounds having certain vinylthio substituents at the 3-position of cephalosporin derivatives are disclosed more recently (U.K. Pat. No. 2,144,420A).

However, known cephalosporin drugs for oral administration are much inferior to the cephalosporin drugs for injectional administration in terms of antibacterial activity and antibacterial spectrum, and the problem is the remarkable increase of resistance strains to these drugs.

Under such circumstances, it is desired to discover cephalosporin drugs having excellent antibacterial activity, wide antibacterial spectrum, and absorption in effective amounts into the blood concentration.

SUMMARY OF THE INVENTION

As a result of the intensive research for the purpose of finding of cephalosporin derivatives showing strong antibacterial activity, wide antibacterial spectrum and high blood concentration when administered orally, the present inventors have discovered a group of cephalosporin derivatives showing superior antibacterial activity, antibacterial spectrum and absorption into the blood in concentrations to cefalexin, and completed the present invention.

The compounds of the present invention are cephalosporin derivatives represented by the general formula

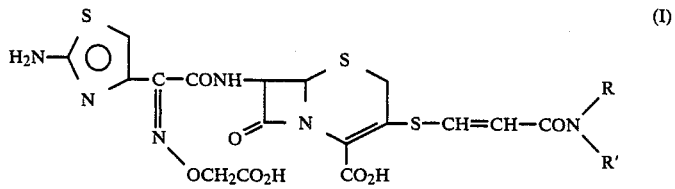

(I)

wherein R represents a hydrogen atom or a lower alkyl group having 1 to 4 carbon atoms, R' represents a hydrogen atom, a lower alkyl group having 1 to 4 carbon atoms, a cycloalkyl group having 5 or 6 carbon atoms or a benzyl group, or R and R' together with the nitrogen atom to which they are attached form a tetrahydropyridinyl group, a morpholinyl group or pyrrolidinyl group, and the non-toxic salts thereof.

DETAILED DESCRIPTION OF THE INVENTION

The terminology "lower alkyl group having 1 to 4 carbon atoms", in the definition of R and R', is intended to include both straight and branched chains groups, for example, a methyl group, an ethyl group, a n-propyl group, an isopropyl group, a n-butyl group, an isobutyl group. The cycloalkyl group refers to a cyclopentyl group and a cyclohexyl group.

"Non-toxic salts", as used herein, has reference to those salts which are pharmaceutically acceptable, for example, salts with inorganic bases including sodium, potassium, calcium and magnesium; salts with organic bases such as ammonia, triethylamine and cyclohexylamine; salts with basic amino acids such as arginine and lysine; salts with mineral acids such as sulfuric acid, hydrochloric acid and phosphoric acid; and salts with organic acids such as acetic acid, lactic acid, tartaric acid, fumaric acid, maleic acid, trifluoroacetic acid and methanesulfonic acid.

Among the preferred compounds of Formula I are included the compounds wherein R represents a hydrogen atom or methyl group and R' represents a hydrogen atom, a methyl group or an ethyl group.

The compounds of the present invention are those in the forms of geometric isomers [E-form and Z-form] derived from the oxyimino group at the 7-position side chain and the vinyl group at the 3-position side chain, respectively, and both isomers are included within the scope of the present invention, but the Z-form derived from the oxyimino group at the 7-position side chain is preferred.

The compounds of Formula I of the present invention can be, for example, obtained according to the following synthetic methods.

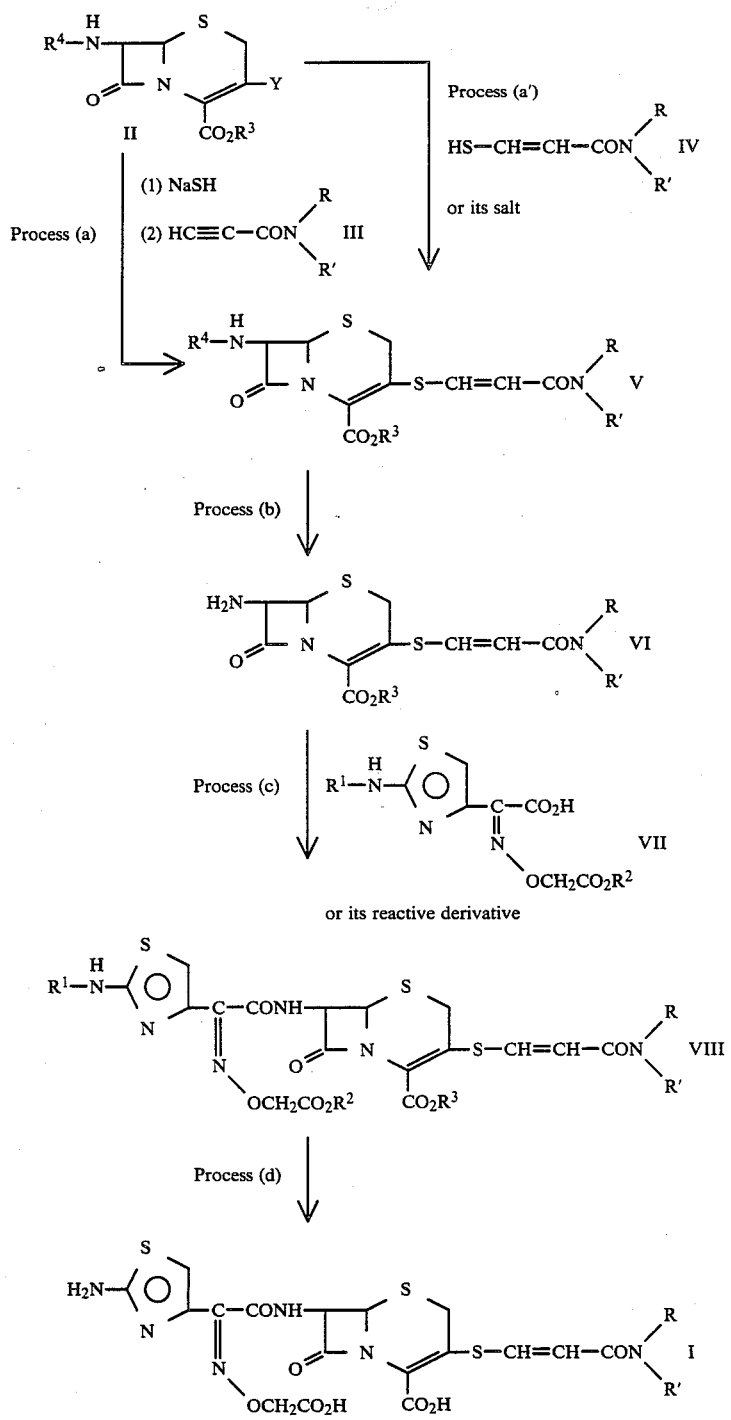

In the scheme mentioned above, R and R' are as defined above, $R^1$ represents a protecting group for the amino group, $R^2$ and $R^3$ represent each a protecting group for the carboxyl group, $R^4$ represents a protecting group for the amino group such as a phenylacetyl group, a phenoxyacetyl group, a trityl group, a phthaloyl group, a formyl group, a benzoyl group, a 2,2,2-trichloroethoxycarbonyl group and the like, Y represents a halogen atom (e.g., a chlorine atom, a bromine atom or an iodine atom), a methanesulfonyloxy group, a trifluoromethanesulfonyloxy group, a diphenylphosphoryloxy group, a p-toluenesulfonyloxy group and the like.

The protecting groups of the amino group and carboxyl group such as $R^1$, $R^2$ and $R^3$ are those frequently used in the field of the β-lactam chemistry. For example, $R^1$ may be trityl group, a monochloroacetyl group, a formyl group, a p-methoxybenzyloxycarbonyl group or the like, and $R^2$ and $R^3$ may each be a benzhydryl group, a p-methoxybenzyl group, p-nitrobenzyl group, a benzyl group, 2,2,2-trichloroethyl group, a trimethylsilyl group, an allyl group or the like.

Process (a): (1) A known compound of Formula II is dissolved in a reaction-inert organic solvent, and reacted with 1.0 to 1.2 molar equivalents of sodium hydrosulfide in the presence of a base to give a 3-mercapto derivative. The reaction temperature is from −50° C. to 100° C., preferably from −25° to 5° C. The reaction time is from 10 minutes to 4 hours, preferably from 10 minutes to one hour.

(2) To the resulting mercapto derivative obtained in the above item (1) is added 1.0 to 2.0 molar equivalents of the compound of Formula III, and the mixture is stirred in the presence of a base at a reaction temperature from −50° C. to 100° C., preferably −25° C. to 60° C. to give a 3-thio substituent of Formula V. The reaction time depends on the kinds of the base and the compound of Formula III which are used, and the reaction temperature, but usually it is in the range of 30 minutes to 30 hours. The preferred solvents in the items (1) and (2) are N,N-dimethylformamide, N,N-dimethylacetamide, dimethyl sulfoxide, hexamethylphosphoramide, acetonitrile, tetrahydrofuran, dichloromethane, chloroform, methanol and mixtures thereof. The preferred base is an organic base such as diisopropylethylamine, N,N-dimethylaminopyridine, N,N-dimethylaniline, triethylamine or the like. The most preferred amount of the base is from 0.2 to 1.5 molar equivalents relative to the compound of Formula II.

The processes (1) and (2) also can be carried out in the same reaction system without isolation of the 3-mercapto derivative obtained in the process (1).

Process (a'): The compound of Formula V also can be obtained by reaction of the compound of Formula II with the compound of Formula IV or a salt thereof. Examples of the salts of the compound of Formula IV are salts with metals such as silver, sodium, potassium, calcium, magnesium and the like. For example, where the silver salt is used as a salt of the compound of Formula IV, the salt is dissolved or suspended in a reaction-inert solvent, and sodium iodide or sodium isocyanate is added in 1.0 to 10 molar equivalents, preferably 4 to 7 molar equivalents, and the mixture is stirred at −20° to 50° C., preferably −5° to 30° C. for one minute to one hour, preferably 5 to 30 minutes.

And then, to the above reaction mixture is added 0.7 to 1.1 molar equivalents of the compound of Formula II in the form of a solid or a solution in the reaction-inert solvent as described below, and the mixture is stirred at a reaction temperature of from −50° to 50° C., preferably from −30° to 20° C. The reaction time is from 5 minutes to 2 hours, preferably from 10 minutes to one hour. Examples of the preferred reaction-inert solvent used in this reaction are acetone, chloroform, dichloromethane, tetrahydrofuran, acetonitrile, diethyl ether, methanol, ethanol, benzene, N,N-dimethylformamide, N,N-dimethylacetamide, dimethyl sulfoxide, hexamethylphosphoramide, dimethyl sulfoxide, hexamethylphosphoramide, water and mixtures thereof.

When the compound of Formula IV is used in the form of a free thiol, the reaction can be carried out in the presence of a base under the same reaction conditions as described above. Examples of preferred bases used in this reaction are diisopropylethylamine, triethylamine, N,N-dimethylaminopyridine, N,N-dimethylaniline and the like. The most preferred amount of the base is from 1.0 to 2.0 molar equivalents relative to the Compound II.

Process (b): The protecting group $R^4$ at the 7-position of the compound of Formula V obtained in the above process (a) or (a') can be eliminated by a method conventionally used in the field of the β-lactam chemistry to give the compound of Formula VI. For example, the compound of Formula V, wherein the protecting group $R^4$ is a phenoxyacetyl group, a phenylacetyl group or a benzoyl group, is dissolved in dichloromethane or benzene, and 1.5 to 2.0 molar equivalents of phosphorus pentachloride and 2.0 to 3.0 molar equivalents of pyridine are added, and then the mixture is stirred at −40° C. to 30° C. for 30 minutes to 3 hours. Subsequently, a large excess amount of methanol is added at −60° C. to 20° C., and the mixture is stirred for 30 minutes to 2 hours. After addition of a large excess amount of water, the mixture is stirred at −50° C. to 20° C. for 30 minutes to one hour to give the compound of Formula VI.

A compound of Formula V, wherein the protecting group $R^4$ is a trityl group, is dissolved in a reaction-inert solvent (e.g., ethyl acetate), 1.0 to 1.5 molar equivalents of p-toluenesulfonic acid monohydrate is added under ice-cooling, and the mixture is stirred for 1 to 5 hours to give the compound of Formula VI in the form of p-toluenesulfonic acid salt. If necessary, the p-toluene sulfonic acid salt is treated with a base to give the compound of Formula VI in the form of the free base.

The compound of Formula V, wherein the protecting group $R^4$ is a 2,2,2-trichloroethoxycarbonyl group, is dissolved in a reaction-inert solvent (e.g., tetrahydrofuran, N,N-dimethylformamide or a mixture thereof), 1.0 to 15 molar equivalents of zinc is added in the presence of ammonium chloride or formic acid under ice-cooling, and the mixture is stirred for 1 to 5 hours to give the compound of Formula VI.

Process (c): In order to obtain the compound of Formula VIII from the compound of Formula VI, the compound of Formula VI is reacted with the 2-aminothiazoleacetic acid derivative of Formula VII in the presence of a condensing agent or reacted with a reactive derivative of the compound of Formula VII. Examples of the condensing agent are N,N'-dicyclohexylcarbodiimide, 1-ethoxycarbonyl-2-ethoxy-1,2-dihydroquinoline, N,N'-carbonyldiimidazole, diphenylphosphoryl azide, Vilsmeier reagent and the like. Examples of the above reactive derivative of the compound of Formula VII are the acid halides (e.g., acid chloride and acid bromide), acid anhydride (e.g., symmetrical acid anhydrides of the compound of Formula VII), and mixed acid anhydrides with ethyl carbonate, diphenylphosphoric acid, methanesulfonic acid and the like, and activated ester (e.g., esters with p-nitrophenyl, thiophenol, N-hydroxysuccinimide and the like).

Referring to the use of an acid chloride as the reactive derivative of the compound of Formula VII, first the compound of Formula VII is dissolved in a reaction-inert solvent, 1.0 to 1.1 molar equivalents of phosphorus pentachloride is added in the presence of a base at −30° C. to −10° C., and the mixture is stirred for 10 to 30 minutes to prepare the acid chloride of the compound of Formula VII. To this compound is added a solution of 0.6 to 1.0 molar equivalent of the compound of Formula VI in the same reaction-inert solvent as those mentioned above in the range of −30° C. to 0° C., and the mixture is stirred for 10 to 30 minutes to give the compound of Formula VIII. Preferred solvents used in this process are dichloromethane, chloroform, acetonitrile, N,N-dimethylformamide and the like. Preferred bases are pyridine, triethylamine, N,N-dimethylaminopyridine, N,N-dimethylaniline, diisopropylethylamine and the like. The amount of the base used is 4.0 to 5.5 molar equivalents relative to the compound Formula VI.

Process (d): The protection groups of the compound of Formula VIII are eliminated by a method conventionally used in the field of the β-lactam chemistry. For example, the compound of Formula VIII is treating with a deprotecting agent [e.g., a large excess amount of trifluoroacetic acid-anisole (volume ratio, 5:1)] in a reaction-inert solvent (e.g., dichloromethane, chloroform, acetic acid and the like) or in the absence of solvent with stirring for 30 minutes to one hour, preferably at −5° C. to 25° C. to give the compound of Formula I.

The compounds of Formula I of the present invention show not only strong antibacterial activity against various pathogenic bacteria but also high absorption in the blood by oral administration, therefore these compounds are useful as antibacterial agents for oral administration. For such purposes, they may be administered orally in a conventional form such as tablets, capsules, granules and the like which can be prepared according to usual pharmaceutical practices. In the above preparations are included conventional additives such as fillers, binding agents, disintegrators, vehicles, pH adjusting agents, solubilizers and the like.

Although the dosage of the compounds of the present invention depends on the age and conditions of the patient, usual dosage is from 200 mg to 1000 mg per person per day.

Subsequently, there were determined the minimal inhibitory concentration (MIC) of the compounds of the present invention against various bacteria and the concentration of the compound in blood after oral administration to rats, and the results are shown below.

Test 1

The antibacterial activity of the compounds of the present invention against various bacteria (inoculum size: $10^6$ cells/ml) were tested by the agar plate dilution method, and the results are shown in the following Table 1.

TABLE 1

| Bacteria | MIC (μg/ml) Test compound | | | |
|---|---|---|---|---|
| | A | B | C | YY |
| Escherichia coli NIHJ JC-2 | 0.2 | 0.39 | 0.2 | 12.5 |
| Klebsiella pneumoniae IFO 3317 | 0.05 | 0.05 | 0.05 | 6.25 |
| Proteus mirabilis IFO 3849 | <0.025 | 0.025 | 0.025 | 12.5 |
| Serratia marcescens IID 618 | 0.2 | 0.39 | 0.39 | >100 |

Note
A: The compound obtained in Example 1
B: The compound obtained in Example 6
C: The compound obtained in Example 8
YY: Cefalexin (previously known compound)

Test 2

Male wister rats (7 weeks old) were administered orally with the test compound, and the change of the concentration of the compound in blood was measured.

| Dosage of the test compound: | 50 mg/kg |
|---|---|
| Quantitative method: | Bioassay |

(test bacterium: Escherichia coli SC507)

The results are shown in Table 2.

TABLE 2

| Time | Concentration in blood (μg/ml) Test compound | | |
|---|---|---|---|
| | B | C | YY |
| One Hour | 26.78 | 20.77 | 17.87 |
| Two Hours | 34.32 | 26.55 | 18.92 |
| Four Hours | 24.17 | 22.40 | 6.71 |

Note
B, C and YY are as defined above.

The present invention is illustrated in more detail by the following Examples but is not intended to be limited thereto.

EXAMPLE 1

(a) To a solution of 16.4 g (21.9 mM) of benzhydryl 7β-phenoxyacetamido-3-diphenylphosphoryloxy-3-cephem-4-carboxylate in 128 ml of N,N-dimethylformamide were added at −10° C. a solution of 1.93 g (24.1 mM) of 70% sodium hydrosulfide in 86 ml of N,N-dimethylformamide and 4.25 g (32.9 mM) of diisopropylethylamine, and the mixture was stirred for 45 minutes. After the reaction, 200 ml of water was added and the mixture was extracted with 200 ml of diethyl ether. The aqueous layer was adjusted to pH 2 to 3 with 0.5% hydrochloric acid and extracted with ethyl acetate (300 ml), and the extract was washed with a saturated aqueous sodium chloride solution (200 ml×2) and dried over anhydrous magnesium sulfate. The solvent was evaporated and the residue was chromatographed over silica gel column (eluent; ethyl acetate:benzene=1:2 to 2:1) to give 10.4 g of benzhydryl 7β-phenoxyacetamido-3-mercapto-3-cephem-4-carboxylate.

To a solution of 1064 mg (2 mM) of benzhydryl 7β-phenoxyacetamido-3-mercapto-3-cephem-4-carboxylate in a mixture of 8 ml of chloroform and 16 ml of methanol were added at room temperature 232 mg (2.4 mM) of N,N-dimethylpropiolamide and 80 mg (0.62 mM) of diisopropylethylamine, and the mixture was stirred for 2.5 hours. After the reaction, 100 ml of 0.5% hydrochloric acid was added, the mixture was extracted with 150 ml of ethyl acetate, and the extract was washed with 100 ml of a saturated aqueous sodium chloride solution and dried over anhydrous magnesium sulfate. The solvent was evaporated and the residue was chromatographed over silica gel column (eluent; ethyl acetate:benzene=1:1) to give 600 mg of benzhydryl 7β-phenoxyacetamido-3-[(Z)-2-N,N-dimethylaminocarbonylvinylthio]-3-cephem-4-carboxylate.

NMR (CDCl$_3$) δ(ppm); 2.98(2H, s), 3.00(3H, s), 3.49(1H, d, J=17 Hz), 3.79 (1H, d, J=17 Hz), 4.58(2H, s), 5.07(1H, d, J=5 Hz), 5.93(1H, dd, J=9 Hz, 5 Hz), 6.12(1H, d, J=10 Hz), 6.70(1H, d, J=10 Hz), 6.89–7.10(4H, m), 7.22–7.47(13H, m).

IR $\nu_{max}^{KBr}$ cm$^{-1}$: 3290, 1780, 1700, 1620, 1480, 1370, 1210, 1150.

(b) To a cooled (−30° C.) solution of 750 mg (1.19 mM) of benzhydryl 7β-phenoxyacetamido-3-[(Z)-2-N,N-dimethylaminocarbonylvinylthio]-3-cephem-4-carboxylate in 14 ml of dry dichloromethane were added 283 mg (3.57 mM) of pyridine and 497 mg (2.38 mM) of phosphorus pentachloride, and the reaction temperature was raised to room temperature for a period of 30 minutes, and the mixture was stirred at the same temperature for one hour. To the cooled (−60° C.) reaction the mixture was added 7 ml of dry methanol, and the temperature of mixture was raised to 0° C. for a period of one hour. Upon continued cooling of the reaction mixture to −50° C., 7 ml of water was added, and the mixture was stirred under ice-cooling for 45 minutes. The reaction mixture was made weakly basic by addition of a saturated aqueous sodium bicarbonate solution, and extracted with 50 ml of ethyl acetate, and the extract was washed with 50 ml of a saturated aqueous sodium chloride solution and dried over anhydrous magnesium sulfate. The solvent was evaporated and the residue was chromatographed over silica gel column (eluent; ethyl acetate:benzene=1:1 to 2:1) to give 292 mg of benzhydryl 7β-amino-3-[(Z)-2-N,N-dimethylaminocarbonylvinylthio]-3-cephem-4-carboxylate.

NMR (CDCl$_3$) δ(ppm); 1.76(2H, bs), 2.98(3H, s), 3.00(3H, s), 3.48(1H, d, J=18 Hz), 3.79(1H, d, J=18 Hz), 4.77(1H, d, J=5 Hz), 4.99(1H, d, J=5 Hz), 6.10(1H, d, J=10 Hz), 6.72(1H, d, J=10 Hz), 7.00(1H, s), 7.21–7.46(10H, m).

IR $\nu_{max}^{Kbr}$ cm$^{-1}$: 2910, 1770, 1720, 1620, 1335, 1265, 1215, 1140.

(c) To a cooled (−15° C.) solution of 539 mg (0.82 mM) of α-(2-tritylaminothiazole-4-yl)-α-[(Z)-benzhydryloxycarbonylmethoxyimino]acetic acid in 15 ml of dry dichloromethane were added 327 mg (4.10 mM) of pyridine and 172 mg (0.82 mM) of phosphorus pentachloride, and the mixture was stirred for 15 minutes. Then, 272 mg (0.55 mM) of benzhydryl 7β-amino-3-[(Z)-2-N,N-dimethylaminocarbonylvinylthio]-3-cephem-4-carboxylate obtained in the above process (b) was added to the mixture at the same temperature, and the mixture was stirred for 15 minutes. After the reaction, 30 ml of 0.5% hydrochloric acid was added, the mixture was extracted with 50 ml of ethyl acetate, and the extract was washed with 30 ml of a saturated aqueous sodium chloride solution and dried over anhydrous magnesium sulfate. The solvent was evaporated and the residue was chromatographed over silica gel column (eluent; ethyl acetate:benzene=1:3 to 1:2) to give 375 mg of benzhydryl 7β-{α-(2-tritylaminothiazole-4-yl)-α-[(Z)-benzhydryloxycarbonylmethoxyimino]acetamido}-3-[(Z)-2-N,N-dimethylaminocarbonylvinylthio]-3-cephem-4-carboxylate.

NMR (CDCl$_3$) δ(ppm); 3.00(3H, s), 3.02(3H, s), 3.24(1H, d, J=17 Hz), 3.62 (1H, d, J=17 Hz), 4.89(1H, d, J=17 Hz), 5.03(1H, d, J=5 Hz), 5.06(1H, d, J=17 Hz), 5.94(1H, dd, J=9 Hz, 5 Hz), 6.07(1H, d, J=10 Hz), 6.63(1H, d, J=10 Hz), 6.80(1H, s), 6.96(1H, s), 7.01(2H, bs), 7.24–7.48(35H, m), 8.03(1H, d, J=9 Hz).

IR $\nu_{max}^{KBr}$ cm$^{-1}$: 3220, 3000, 2900, 1780, 1720, 1620, 1475, 1360, 1265, 1210.

(d) To a mixture of 4.5 ml of trifluoroacetic acid and 0.9 ml of anisole was added under ice-cooling 360 mg ) 0.32 mM) of benzhydryl 7β-{α-(2-tritylaminothiazole-4-yl)-α-[(Z)-benzhydryloxycarbonylmethoxyimino]acetamido}-3-[(Z)-2-N,N-dimethylaminocarbonylvinylthio-3-cephem-4-carboxylate, and the mixture was stirred for 40 minutes. The reaction mixture was slowly added dropwise to a mixture of diethyl ether and n-hexane (1:2, 40 ml), and the formed crystals were collected by filtration to give 205 mg of 7β-{α-(2-aminothiazole-4-yl)-α-[(Z)-carboxymethoxyimino]acetamido}-3-[(Z)-2-N,N-dimethylaminocarbonylvinylthio]-3-cephem-4-carboxylic acid trifluoroacetate. Then, the crystals and 80 mg (0.96 mM) of sodium bicarbonate were dissolved in 5 ml of water, and the solution was chromatographed over Sephadex LH-20 column (eluent; water) to give 165 mg of 7β-{α-(2-aminothiazole-4-yl)-α-[(Z)-carboxymethoxyimino]acetamido}-3-[(Z)-2-N,N-dimethylaminocarbonylvinylthio]-3-cephem-4-carboxylic acid sodium salt.

NMR (D$_2$O) δ(ppm); 1.99(3H, s), 2.12(3H, s), 3.58(1H, d, J=17 Hz), 3.96(1H, d, J=17 Hz), 4.61(2H, s), 5.32(1H, d, J=5 Hz), 5.89(1H, d, J=5 Hz), 6.48(1H, d, J=10 Hz), 7.09(1H, d, J=10 Hz), 7.10(1H, s).

IR $\nu_{max}^{KBr}$ cm$^{-1}$: 3280, 1755, 1600, 1385, 1145.

EXAMPLE 2

(a) To a solution of 3500 mg (4.7 mM) of benzhydryl 7β-phenoxyacetamido-3-diphenylphosphoryloxy-3-cephem-4-carboxylate in 28 ml of N,N-dimethylformamide were added at −10° C. a solution of 412 mg (5.1 mM) of 70% sodium hydrosulfide in 18 ml of N,N-dimethylformamide and 908 mg (7.1 mM) of diisopropylethylamine, and the mixture was stirred for 30 minutes. 1050 mg (9.4 mM) of N,N-diethylpropiolamide was added, and then the mixture was stirred at room temperature for 20 hours and at 55° C. for 1.5 hours. After the reaction, 100 ml of 0.5% hydrochloric acid was added, the mixture was extracted with 200 ml of ether acetate, and the extract was washed with a saturated aqueous sodium chloride solution (150 ml×2) and dried over anhydrous magnesium sulfate. The solvent was evaporated and the residue was chromatographed over silica gel column (eluent; ethyl acetate:benzene=1:2 to 1:1) to give 590 mg of benzhydryl 7β-phenoxyacetamido-3-[(Z)-2-N,N-diethylaminocarbonylvinylthio]-3-cephem-4-carboxylate.

NMR (CDCl$_3$) δ(ppm); 1.16(3H, t, J=7 Hz), 1.17(3H, t, J=7 Hz), 3.30(2H, q, J=7 Hz), 3.38–3.52(2H, m), 3.50(1H, d, J=17 Hz), 3.80(1H, d, J=17 Hz), 4.58(2H, s), 5.08(1H, d, J=5 Hz), 5.94(1H, dd, J=9 Hz), 6.08(1H, d, J=10 Hz), 6.70(1H, d, J=10 Hz), 6.90–7.12(4H, m), 7.22–7.48(13H, m).

IR $\nu_{max}^{KBr}$ cm$^{-1}$: 3300, 2920, 1780, 1685, 1615, 1490, 1365, 1260, 1215.

(b) To a cooled (−35° C.) solution of 740 mg (1.1 mM) of benzhydryl 7β-phenoxyacetamido-3-[(Z)-2-N,N-diethylaminocarbonylvinylthio]-3-cephem-4-carboxylate, obtained in the above process (a), in 14 ml of dry dichloromethane were added 268 mg (3.3 mM) of pyridine and 469 mg (2.2 mM) of phosphorus pentachloride, the reaction temperature was raised to room temperature for a period of 30 minutes, and the mixture was stirred at the same temperature for 1.5 hours. To the cooled (−60° C.) reaction mixture was added 7 ml of dry methanol, and the temperature of the mixture was raised to 0° C. for a period of one hour. Upon continued cooling of the reaction mixture to −50° C., 7 ml of water was added, and the mixture was stirred under ice-cooling for 45 minutes. The reaction mixture was made weakly basic by addition of a saturated aqueous sodium bicarbonate solution, and extracted with 50 ml of ethyl acetate, and the extract was washed with 50 ml of a saturated aqueous sodium chloride solution and dried over anhydrous magnesium sulfate. The solvent was evaporated and the residue was chromatographed over silica gel column (eluent; ethyl acetate:benzene=1:1 to 2:1) to give 329 mg of benzhydryl 7β-amino-3-[(Z)-2-N,N-diethylaminocarbonylvinylthio]-3-cephem-4-carboxylate.

NMR (CDCl$_3$) δ(ppm); 1.16(3H, t, J=7 Hz), 1.18(3H, t, J=7 Hz), 1.84(2H, bs), 3.30(2H, q, J=7 Hz), 3.38–3.53(2H, m), 3.50(1H, d, J=18 Hz), 3.78(1H, d, J=18 Hz), 4.79(1H, d, J=5 Hz), 4.99(1H, d, J=5 Hz), 6.07(1H, d, J=10 Hz), 6.73(1H, d, J=10 Hz), 7.00(1H, s), 7.22–7.46(10H, m).

IR $\nu_{max}^{KBr}$ cm$^{-1}$: 3360, 2960, 1770, 1720, 1610, 1445, 1355, 1260, 1210.

(c) To a cooled (−10° C.) solution of 410 mg (0.63 mM) of α-(2-tritylaminothiazole-4-yl)-α-[(Z)-benzhydryloxycarbonylmethoxyimino]acetic acid in 13 ml of dry dichloromethane were added 248 mg (3.15 mM) of pyridine and 131 mg (0.63 mM) of phosphorus pentachloride, and the mixture was stirred for 20 minutes. Then, 300 mg (0.57 mM) of benzhydryl 7β-amino-3-[(Z)-2-N,N-diethylaminocarbonylvinylthio]-3-cephem-4-carboxylate obtained in the above process (b) was added to the mixture at the same temperature, and the mixture was stirred for 20 minutes. After the reaction, 30 ml of 0.5% hydrochloric acid was added, the mixture was extracted with 50 ml of ethyl acetate, and the extract was washed with 30 ml of a saturated aqueous sodium chloride solution and dried over anhydrous magnesium sulfate. The solvent was evaporated and the residue was chromatographed over silica gel column (eluent; ethyl acetate:benzene=1:2 to 1:1) to give 400 mg of benzhydryl 7β-{α-(2-tritylaminothiazole-4-yl)-α-[(Z)-benzhydryloxycarbonylmethoxyimino]acetamido}-3-[(Z)-2-N,N-diethylaminocarbonylvinylthio]-3-cephem-4-carboxylate.

NMR (CDCl$_3$) δ(ppm); 1.17(3H, t, J=7 Hz), 1.18(3H, t, J=7 Hz), 3.25(1H, d, J=17 Hz), 3.30(2H, q, J=7 Hz), 3.38–3.53(2H, m), 3.62(1H, d, J=17 Hz), 4.88(1H, d, J=17 Hz), 5.03(1H, d, J=5 Hz), 5.06(1H, d, J=17 Hz), 5.93(1H, dd, J=9 Hz, 5 Hz), 6.03(1H, d, J=10 Hz), 6.61(1H, d, J=10 Hz), 6.80(1H, s), 6.96(1H, s), 7.00(2H, s), 7.22–7.46(35H, m), 8.04(1H, d, J=9 Hz).

IR $\nu_{max}^{KBr}$ cm$^{-1}$: 3260, 1780, 1730, 1680, 1615, 1510, 1360, 1260, 1210.

(d) To a mixture of 4.5 ml of trifluoroacetic acid and 0.9 ml of anisole was added under ice-cooling 360 mg (0.31 mM) of benzhydryl 7β-{α-(2-tritylaminothiazole-4-yl-α-[(Z)-benzhydryloxycarbonylmethoxyimino]acetamido}-3-[(Z)-2-N,N-diethylaminocarbonylvinylthio]-3-cephem-4-carboxylate, and the mixture was stirred for 40 minutes. The reaction mixture was slowly added dropwise to a mixture of diethyl ether and n-hexane (1:2, 40 ml), and the formed crystals were collected by filtration to give 210 mg of 7β-{α-(2-aminothiazole-4-yl)-α-[(Z)-carboxymethoxyimino]acetamido}-3-[(Z)-2-N,N-diethylaminocarbonylvinylthio]-3-cephem-4-carboxylic acid trifluoroacetate. Then, the crystals and 78 mg (0.93 mM) of sodium bicarbonate were dissolved in 5 ml of water, and the solution was chromatographed over Sephadex LH-20 column (eluent; water) to give 160 mg of 7β-{α-(2-aminothiazole-4-yl)-α-[(Z)-2-carboxymethoxyimino]acetamido}-3-[(Z)-2-N,N-dithylaminocarbonylvinylthio]-3-cephem-4-carboxylic acid sodium salt.

NMR (D$_2$O) δ(ppm); 1.16(3H, t, J=7 Hz), 1.22(3H, t, J=7 Hz), 3.45(1H, q, J=7 Hz), 3.49(2H, q, J=7 Hz), 3.60(1H, d, J=17 Hz), 3.98(1H, d, J=17 Hz), 4.63(2H, s), 5.33(1H, d, J=5 Hz), 5.91(1H, d, J=5 Hz), 6.48(1H, d, J=10 Hz), 7.10(1H, s), 7.12(1H, d, J=10 Hz).

IR $\nu_{max}^{KBr}$ cm$^{-1}$: 3300, 1755, 1595, 1345, 1260.

EXAMPLES 3-5

Following the procedures and reaction conditions of Example 1, there were obtained the following compounds indicated in Table 3 by using N-propionyl 1,2,3,6-tetrahydropyridine, N-propionylpyrroridine and N-propionylmorpholine, respectively, in place of N,N-dimethylpropiolamide.

TABLE 3

| Example No. | −N⟨R/R' | NMR(D$_2$O) δ(ppm) | IR $\nu_{max}^{KBr}$ cm$^{-1}$ |
|---|---|---|---|
| 3 | −N (tetrahydropyridine) | 2.14~2.32(2H, m)<br>3.58(1H, d, J=17 Hz)<br>3.61~3.75(2H, m)<br>3.96(1H, d, J=17 Hz)<br>4.01~4.16(2H, m)<br>4.60(2H, s)<br>5.32(1H, d, J=5 Hz)<br>5.69~6.04(2H, m)<br>6.40~6.59(1H, m)<br>7.08(1H, s)<br>7.12(1H, d, J=10 Hz) | 3350<br>1755<br>1665<br>1595<br>1525<br>1380<br>1200 |
| 4 | −N (pyrrolidine) | 1.80~2.08(4H, m)<br>3.40~3.66(4H, m)<br>3.58(1H, d, J=17 Hz)<br>3.96(1H, d, J=17 Hz)<br>4.60(2H, s)<br>5.31(1H, d, J=5 Hz)<br>5.88(1H, d, J=5 Hz)<br>6.32(1H, d, J=10 Hz)<br>7.08(1H, d, J=10 Hz)<br>7.08(1H, s) | 3280<br>1755<br>1600<br>1525<br>1335 |
| 5 | −N O (morpholine) | 3.57(1H, d, J=17 Hz)<br>3.58~3.82(8H, m)<br>3.95(1H, d, J=17 Hz)<br>4.80(2H, s)<br>5.31(1H, d, J=5 Hz)<br>5.88(1H, d, J=5 Hz)<br>6.47(1H, d, J=10 Hz)<br>7.08(1H, s)<br>7.15(1H, d, J=10 Hz) | 3320<br>1760<br>1600<br>1525<br>1375<br>1345<br>1230 |

EXAMPLE 6

(a') To a suspension of 784 mg (3.294 mM) of (Z)-2-(N-ethylcarbamoyl)vinylmercaptan silver salt in 30 ml of acetonitrile was added 2.965 g (19.77 mM) of sodium iodide, and the mixture was stirred at room temperature for 5 minutes. To the mixture was added at 0° C. a solution of 2 g (2.53 mM) of benzhydryl 7β-2,2,2-trichloroethoxycarbonylamino-3-diphenylphosphoryloxy-3-cephem-4-carboxylate in 20 ml of acetonitrile, and the mixture was stirred at the same temperature for 30 minutes, and then some insoluble material was filtered. To the filtrate was added 100 ml of ethyl acetate, and the mixture was washed with a saturated aqueous sodium chloride solution (50 ml×3) and dried over anhydrous magnesium sulfate. The solvent was evaporated and the residue was chromatographed over silica gel column (eluent; chloroform) to give 1.65 g of benzhydryl 7β-2,2,2-trichloroethyoxycarbonylamino-3-[(Z)-2-(N-ethylcarbamoyl)vinylthio]-3-cephem-4-carboxylate.

NMR (CDCl$_3$) δ(ppm); 1.16(3H, t, J=7 Hz), 3.36(2H, dq, J=7 Hz), 3.49(1H, d, J=18 Hz), 3.76(1H, d, J=18 Hz), 4.77(2H, s), 5.05(1H, d, J=5 Hz), 5.56(1H, t, J=7 Hz), 5.64(1H, dd, J=9 Hz, 5 Hz), 5.72(1H, d, J=11

Hz), 5.99(1H, d, J=9 Hz), 6.63(1H, d, J=11 Hz), 6.98(1H, s), 7.22–7.48(10H, m).

IR $\nu_{max}^{KBr}$ cm$^{-1}$: 3350, 1780, 1725, 1635, 1515, 1365, 1120, 1185, 1095.

(b) To a solution of 671 mg (1 mM) of benzhydryl 7β-2,2,2-trichloroethyoxycarbonylamino-3-[(Z)-2-N-ethylcarbamoyl)vinylthio]-3-cephem-4-carboxylate, obtained in the above process (a'), in a mixture of 5.5 ml of tetrahydrofuran and 1.5 ml of N,N-dimethylformamide were added at 0° C. with stirring 654 mg (10 mM) of zinc powder, 1.5 ml of formic acid and 1.5 ml of water, respectively, and then the mixture was stirred at the same temperature for one hour. After separating the insolubles by filtration, the filtrate was made neutral with a saturated aqueous sodium bicarbonate solution and extracted with 50 ml of ethyl acetate, and the extract was washed with 30 ml of a saturated aqueous sodium chloride solution and dried over anhydrous magnesium sulfate. The solvent was evaporated and the residue was chromatographed over silica gel column (eluent; benzene:acetone=5:1) to give 210 mg of benzhydryl 7β-amino-3-[(Z)-2-(N-ethylcarbamoyl)vinyl thio]-3-cephem-4-carboxylate.

NMR (CDCl$_3$) δ(ppm); 1.17(3H, t, J=7 Hz), 3.36(2H, q, J=7 Hz), 3.49(1H, d, J=18 Hz), 3.78(1H, d, J=18 Hz), 4.75(1H, d, J=5 Hz), 4.98(1H, d, J=5 Hz), 5.67(1H, d, J=11 Hz), 6.64(1H, d, J=11 Hz), 7.00(1H, s), 7.23–7.48(10H, m).

IR $\nu_{max}^{KBr}$ cm$^{-1}$: 3220, 3040, 2960, 2910, 1775, 1745, 1690, 1575, 1360, 1270, 1245, 1205, 1170.

(c) Following the procedure and reaction conditions of Example 2(c), there was obtained benzhydryl 7β-{α-(2-tritylaminothiazole-4-yl)-α-[(Z)-benzhydryloxycarbonylmethoxyimino]acetamido}-3-[(Z)-2-(N-ethylcarbamoyl)vinylthio]-3-cephem-4-carboxylate by using the compound obtained in the above process (b).

NMR (CDCl$_3$) δ(ppm); 1.23(3H, t, J=7 Hz), 3.23(1H, d, J=18 Hz), 3.39(2H, dq, J=7 Hz, J=7 Hz), 3.61(1H, d, J=18 Hz), 4.89(1H, d, J=18 Hz), 5.03(1H, d, J=5 Hz), 5.06(1H, d, J=18 Hz), 5.43(1H, t, J=7 Hz), 5.65(1H, d, J=11 Hz), 5.93(1H, dd, J=9 Hz, 5 Hz), 6.56(1H, d, J=11 Hz), 6.81(1H, s), 6.97(1H, s), 7.02(2H, s), 7.20–7.50(35H, m), 8.03(1H, d, J=9 Hz).

IR $\nu_{max}^{KBr}$ cm$^{-1}$: 3380, 1780, 1730, 1680, 1645, 1580, 1520, 1490, 1445, 1370, 1275, 1215, 1180.

(d) Following the procedure and reaction conditions of Example 2(d), there was obtained 7β-{α-(2-aminothiazole-4-yl)-α-[(Z)-carboxymethoxyimino]acetamido}-3-[(Z)-2-(N-ethylcarbamoyl)vinylthio]-3-cephem-4-carboxylic acid sodium salt by using the compound obtained in the above process (c).

NMR (D$_2$O) δ(ppm); 1.12(3H, t, J=7 Hz), 3.27(2H, q, J=7 Hz), 3.58(1H, d, J=18 Hz), 3.96(1H, d, J=18 Hz), 4.61(2H, s), 5.31(1H, d, J=5 Hz), 5.89(1H, d, J=5 Hz), 6.05(1H, d, J=11 Hz), 6.99(1H, d, J=11 Hz), 7.09(1H, s).

IR $\nu_{max}^{KBr}$ cm$^{-1}$: 3250, 1760, 1600, 1525, 1345, 1250, 1185, 1030.

EXAMPLE 7

(a') Following the procedure and reaction conditions of Example 6(a'), there was obtained benzhydryl 7β-tritylamino-3-[(Z)-2-carbamoylvinylthio]-3-cephem-4-carboxylate by using benzhydryl 7β-tritylamino-3-diphenylphosphoryloxy-3-cephem-4-carboxylate and (Z)-2-carbamoylvinylmercaptan silver salt.

NMR (CDCl$_3$) δ(ppm); 2.95(1H, d, J=9 Hz), 3.31(1H, d, J=18 Hz), 3.56(1H, d, J=18 Hz), 4.33(1H, d, J=5 Hz), 4.77(1H, dd, J=9 Hz, 5 Hz), 5.50(2H, bs), 5.70(1H, d, J=11 Hz), 6.66(1H, d, J=11 Hz), 6.94(1H, s), 7.16–7.56(25H, m).

IR $\delta_{max}^{KBr}$ cm$^{-1}$: 3320, 1770, 1725, 1650, 1570, 1475, 1440, 1360, 1265, 1210.

(b) To a solution of 470 mg (0.66 mM) of benzhydryl 7β-tritylamino-3-[(Z)-2-carbamoylvinylthio]-3-cephem-4-carboxylate, obtained in the above process (a), in 10 ml of ethyl acetate was added under ice-cooling 151 mg (0.79 mM) of p-toluenesulfornic acid monohydrate, and the mixture was stirred for 5 hours. After the reaction, the formed white crystals were collected by filtration to give 372 mg of benzhydryl 7β-amino-3-[(Z)-2-carbamoylvinylthio]-3-cephem-4-carboxylate p-toluenesulfonate.

NMR (DMSO-d$_6$) δ(ppm); 2.29(3H, s), 3.90(1H, d, J=18 Hz), 4.10(1H, d, J=18 Hz) 5.25(1H, d, J=5 Hz), 5.34(1H, d, J=5 Hz), 6.14(1H, d, J=11 Hz), 6.94(1H, s), 7.06–7.70(16H, m), 9.13(2H, bs)

IR $\nu_{max}^{KBr}$ cm$^{-1}$: 3500–2200, 1780, 1650, 1380, 1210, 1160, 1120, 1030, 1010.

(c) Following the procedure and reaction conditions of Example 2(c), there was obtained benzhydryl 7β-{α-(2-tritylaminothiazole-4-yl)-α-[(Z)-benzhydryloxycarbonylmethoxyimino]acetamido}-3-[(Z)-2-carbamoylvinylthio]-3-cephem-4-carboxylate by using benzhydryl 7β-amino-3-[(Z)-2-carbamoylvinylthio]-3-cephem-4-carboxylate p-toluenesulfonate obtained in the above process (b).

NMR (CDCl$_3$) δ(ppm); 3.22(1H, d, J=18 Hz), 3.60(1H, d, J=18 Hz), 4.90(1H, d, J=17 Hz), 5.03(1H, d, J=5 Hz), 5.06(1H, d, J=17 Hz), 5.50(2H, bs), 5.74(1H, d, J=11 Hz), 5.93(1H, dd, J=9 Hz, 5 Hz), 6.67(1H, d, J=11 Hz), 6.80(1H, s), 6.96(1H, s), 7.00(1H, s), 7.40(1H, s), 7.20–7.50(35H, m), 8.07(1H, s, J=9 Hz).

IR $\nu_{max}^{KBr}$ cm$^{-1}$: 3380, 1780, 1730, 1650, 1520, 1445, 1320, 1280, 1215.

(d) Following the procedure and reaction conditions of Example 2(d), there was obtained 7β-{α-(2-aminothiazole-4-yl)-α-[(Z)-carboxymethoxyimino]acetamido}-3-[(Z)-2-carbamoylvinylthio]-3-cephem-4-carboxylic acid sodium salt by using benzhydryl 7β-{α-(2-tritylaminothiazole-4-yl)-α-[(Z)-benzhydryloxycarbonylmethoxyimino]acetamido}-3-[(Z)-2-carbamoylvinylthio]-3-cephem-4-carboxylate obtained in the above process (c).

NMR (D$_2$O) δ(ppm); 3.57(1H, d, J=18 Hz), 3.96(1H, d, J=18 Hz), 4.60(2H, s), 5.31(1H, d, J=5 Hz), 5.88(1H, d, J=5 Hz), 6.11(1H, d, J=11 Hz), 7.08(1H, s), 7.10(1H, d, J=11 Hz).

IR $_{max}^{KBr}$ cm$^{-1}$: 3350, 1755, 1650, 1595, 1520, 1385, 1345, 1300, 1190, 1030.

EXAMPLES 8–10

Following the procedures and reaction conditions of Example 7, there were obtained the following compounds indicated in Table 4 by using (Z)-2-(N-methylcarbamoyl)vinylmercaptan silver salt, (Z)-2-(N-cyclohexylcarbamoyl)vinylmercaptan silver salt and (Z)-2-(N-benzylcarbamoyl)vinylmercaptan silver salt, respectively, in place of (Z)-2-carbamoylvinylmercaptan silver salt.

TABLE 4

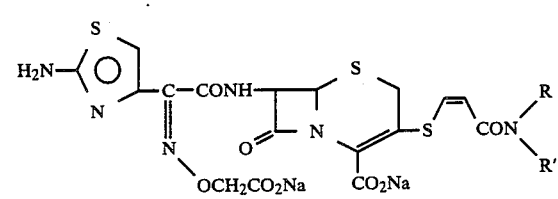

| Example No. | $-N\begin{smallmatrix}R\\R'\end{smallmatrix}$ | NMR(D$_2$O) δ(ppm) | IR $\nu_{max}^{KBr}$ cm$^{-1}$ |
|---|---|---|---|
| 8 | —NHCH$_3$ | 2.78(3H, s) | 3300 |
| | | 3.58(1H, d, J=18 Hz) | 1760 |
| | | 3.96(1H, d, J=18 Hz) | 1600 |
| | | 4.60(2H, s) | 1520 |
| | | 5.31(1H, d, J=5 Hz) | 1385 |
| | | 5.89(1H, d, J=5 Hz) | 1340 |
| | | 6.08(1H, d, J=11 Hz) | 1310 |
| | | 6.99(1H, d, J=11 Hz) | 1250 |
| | | 7.08(1H, s) | 1180 |
| | | | 1030 |
| 9 |  —NH—cyclohexyl | 1.06~1.60(5H, m) | 3260 |
| | | 1.60~1.92(5H, m) | 2910 |
| | | 3.57(1H, d, J=18 Hz) | 2840 |
| | | 3.65(1H, bm) | 1760 |
| | | 3.96(1H, d, J=18 Hz) | 1670 |
| | | 4.61(2H, s) | 1590 |
| | | 5.31(1H, d, J=5 Hz) | 1525 |
| | | 5.89(1H, d, J=5 Hz) | 1385 |
| | | 6.04(1H, d, J=11 Hz) | 1345 |
| | | 6.99(1H, d, J=11 Hz) | 1315 |
| | | 7.08(1H, s) | 1245 |
| | | | 1200 |
| | | | 1175 |
| | | | 1125 |
| | | | 1035 |
| 10 | —NHCH$_2$—phenyl | 3.55(1H, d, J=17 Hz) | 3340 |
| | | 3.94(1H, d, J=17 Hz) | 1760 |
| | | 4.45(2H, s) | 1630 |
| | | 4.61(2H, s) | 1600 |
| | | 5.30(1H, d, J=5 Hz) | 1525 |
| | | 5.88(1H, d, J=5 Hz) | 1385 |

TABLE 4-continued

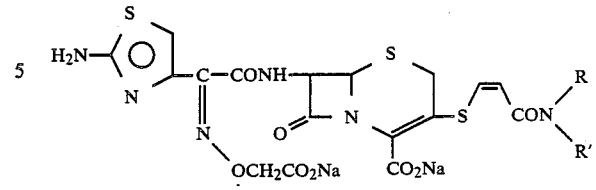

| Example No. | $-N\begin{smallmatrix}R\\R'\end{smallmatrix}$ | NMR(D$_2$O) δ(ppm) | IR $\nu_{max}^{KBr}$ cm$^{-1}$ |
|---|---|---|---|
| | | 6.13(1H, d, J=11 Hz) | 1350 |
| | | 7.05(1H, d, J=11 Hz) | 1320 |
| | | 7.08(1H, s) | 1250 |
| | | 7.30~7.50(5H, m) | 1200 |
| | | | 1175 |
| | | | 1130 |
| | | | 1035 |

What is claimed is:

1. A cephalosporin derivatives represented by the formula

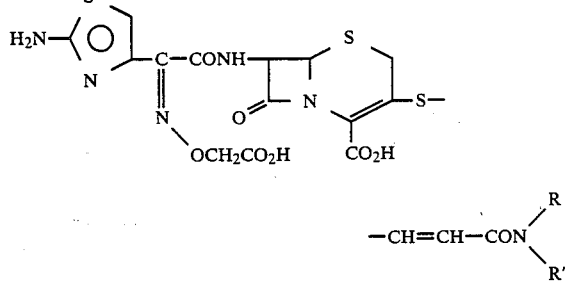

wherein R is a hydrogen atom or a lower alkyl group having 1 to 4 carbon atoms, R' is a hydrogen atom, a lower alkyl group having 1 to 4 carbon atoms, a cycloalkyl group having 5 or 6 carbon atoms or a benzyl group, or R and R' together with the nitrogen atom to which they are attached form a tetrahydropyridinyl group, a morpholinyl group or pyrroridinyl group, and the non-toxic salts thereof.

2. A cephalosporin derivative according to claim 1 wherein R and R' are each a hydrogen atom.

3. A cephalosporin derivative according to claim 1 wherein R and R' are each a methyl group.

4. A cephalosporin derivative according to claim 1 wherein R is a hydrogen atom and R' is a methyl group.

5. A cephalosporin derivative according to claim 1 wherein R is a hydrogen atom and R' is an ethyl group.

* * * * *